United States Patent [19]
Kovacevic et al.

[11] Patent Number: 5,425,775
[45] Date of Patent: Jun. 20, 1995

[54] METHOD FOR MEASURING PATELLOFEMORAL FORCES

[75] Inventors: Nebojsa Kovacevic, Plymouth, Minn.; Kenton Kaufman, El Cajon, Calif.

[73] Assignee: N.K. Biotechnical Engineering Company, Minneapolis, Minn.

[21] Appl. No.: 146,603

[22] Filed: Nov. 2, 1993

Related U.S. Application Data

[63] Continuation-in-part of Ser. No. 902,921, Jun. 23, 1992, abandoned.

[51] Int. Cl.⁶ .............................................. A61B 5/103
[52] U.S. Cl. .................................. 623/20; 623/901; 606/102; 128/774
[58] Field of Search ................. 128/782, 774; 623/20, 623/39, 901; 606/73, 86, 88, 89, 102; 73/862.621, 862.625, 862.627, 862.632, 862.633, 862.635, 862.636, 862.637

[56] References Cited

U.S. PATENT DOCUMENTS

| | | |
|---|---|---|
| 2,992,556 | 7/1961 | Webster . |
| 3,213,400 | 10/1965 | Gieb . |
| 3,335,318 | 8/1967 | Giovanni . |
| 3,341,794 | 9/1967 | Stedman . |
| 3,696,317 | 10/1972 | Farr ........................................ 338/5 |
| 4,166,997 | 9/1979 | Kistler . |
| 4,240,162 | 12/1980 | Devas ...................................... 623/20 |
| 4,583,554 | 4/1986 | Mittleman et al. . |
| 4,795,473 | 1/1989 | Grimes .................................. 623/23 |
| 4,964,867 | 10/1990 | Bogas .................................... 623/20 |
| 4,969,471 | 11/1990 | Daniel et al. ........................ 128/774 |
| 5,019,104 | 5/1991 | Whiteside et al. ................... 623/20 |
| 5,021,061 | 6/1991 | Wevers et al. ....................... 623/20 |
| 5,156,163 | 10/1992 | Watkins et al. . |
| 5,197,488 | 3/1993 | Kovacevic ........................... 128/782 |
| 5,197,986 | 3/1993 | Mikhail ................................ 623/20 |
| 5,236,462 | 8/1993 | Mikhail ................................ 623/20 |

Primary Examiner—Stephen C. Pellegrino
Assistant Examiner—Guy V. Tucker
Attorney, Agent, or Firm—Westman, Champlin & Kelly

[57] ABSTRACT

A method and apparatus for measuring the forces acting on a patella includes a patella sensor comprising a sensor, a sensor cover, and a plurality of strain gages. The sensor cover is attached to the sensor and has an outer surface that is in contact with a femoral insert. The sensor cover transmits the forces acting on its outer surface to the sensor. The sensor has a plurality of strain gages mounted thereon to measure the forces acting on the sensor cover. The sensor is mounted to a resected patella. The measured forces are then used to obtain loading and boundary limits for the design of patellofemoral prosthetic components.

4 Claims, 4 Drawing Sheets

METHOD FOR MEASURING PATELLOFEMORAL FORCES

CROSS REFERENCE TO RELATED APPLICATION

This application is a continuation-in-part of application Ser. No. 07/902,921, filed Jun. 23, 1992, abandoned.

BACKGROUND OF THE INVENTION

The present invention relates to a method and apparatus for sensing the forces on a patellar implant in a human knee, and in particular to a method and apparatus for measuring the forces at the patellofemoral joint.

Advances in surgical technique, instrumentation and prosthesis design have enabled surgeons to achieve some satisfactory results in total knee arthroplasty. Advances have been made in the areas of tibial and femoral alignment and fixation such that the outcome of the femoral and tibial components of total knee arthroplasty has been excellent.

However, the patellofemoral component of total knee arthroplasty has been a source of problems and the patella remains a persistent cause of poor results. Little attention has been focused on the patella, and patellar implant complication is now one of the most frequent causes of total knee arthroplasty failure. Complications affecting the patellofemoral joint occur in up to ten percent of knee arthroplasties and account for up to fifty percent of revision knee procedures. Among the problems documented are postoperative patellar pain, fracture, loosening, subluxation, dislocation, and patellar implant wear.

A major cause of patellar implant complications has been identified as stress at the patellofemoral joint. It is therefore necessary to more accurately measure the forces that act on the patellar implant. While other methods have been used to attempt to measure patellar forces, there is a need for an apparatus which will enable direct measurement of all the forces acting on the patella at the patellofemoral joint.

SUMMARY OF THE INVENTION

The present invention provides an apparatus which is capable of direct measurement of the forces acting on a patellar implant at the patellofemoral joint by measuring the three orthogonal components of the forces. The apparatus as disclosed comprises a base for attaching the apparatus to the patella, a sensor for measuring the orthogonal components of the forces, a sensor cover, and a plurality of strain gages for measuring the component forces.

The sensor disclosed specifically comprises a first disc, a second disc connected to the first disc, a ring-shaped plate, and four supports. Each of the supports has the shape of a rectangular web or thin column and is located between the second disc and the ring-shaped plate. Four strain gages are mounted on the second disc and two strain gages are mounted on each support.

The sensor cover is screwed onto a threaded cylindrical protrusion extending from the first disc so that it covers the protrusion and the first disc. The sensor cover has an outer surface that comes into contact with an artificial femoral attachment.

The sensor is mounted on the base by inserting screws through holes in the plate and in the base. The base is implanted in the patella using three studs which are inserted through holes in the base and are then inserted through holes drilled in the patella. Alternatively, the sensor is attached directly to a resected surface of the patella facing the contact surface of the femur with suitable bone cement and, if desired, mounting studs. Preferably, the sensor cover is positioned and formed similar to the patella prior to resection so that sensor cover, transducer and resected patella simulate a natural patella.

With the force measuring sensor in position, the knee is flexed. The forces acting on the sensor cover are transmitted to the sensor, causing a bowing of the second disc and a flexing of the four supports. These movements are detected and measured by the strain gages and are used to determine the orthogonal components of the forces acting on the sensor cover. The strain gages provide signals proportional to the orthogonal components of the forces acting on the sensor cover to a display and recording instrument. The forces measured provide accurate loading and boundary limits for the design of patellofemoral prosthetic components.

DETAILED DESCRIPTION OF THE PREFERRED EMBODIMENTS

Figure 1:
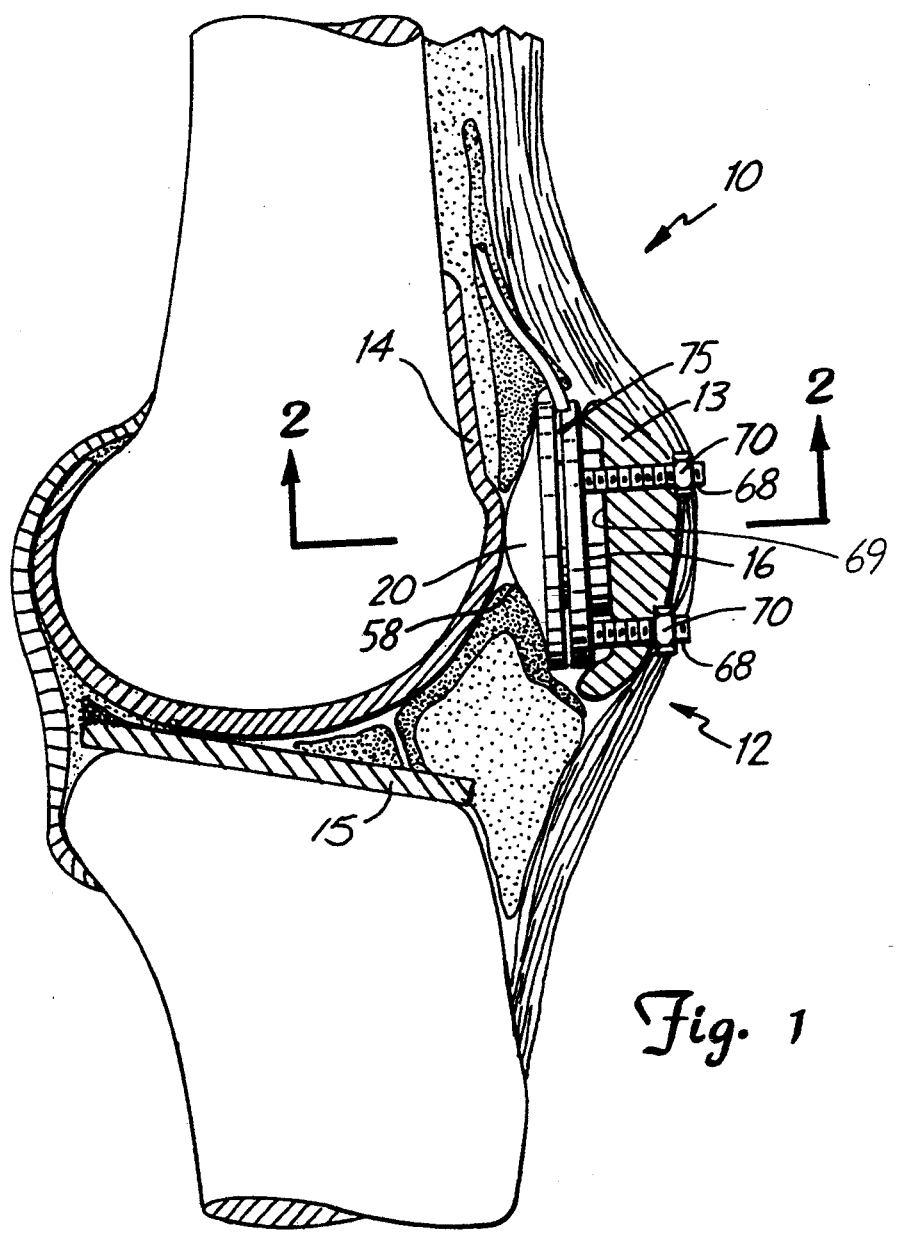
FIG. 1 is a side view of the apparatus of the present invention inserted in a human knee.
Figure 2:
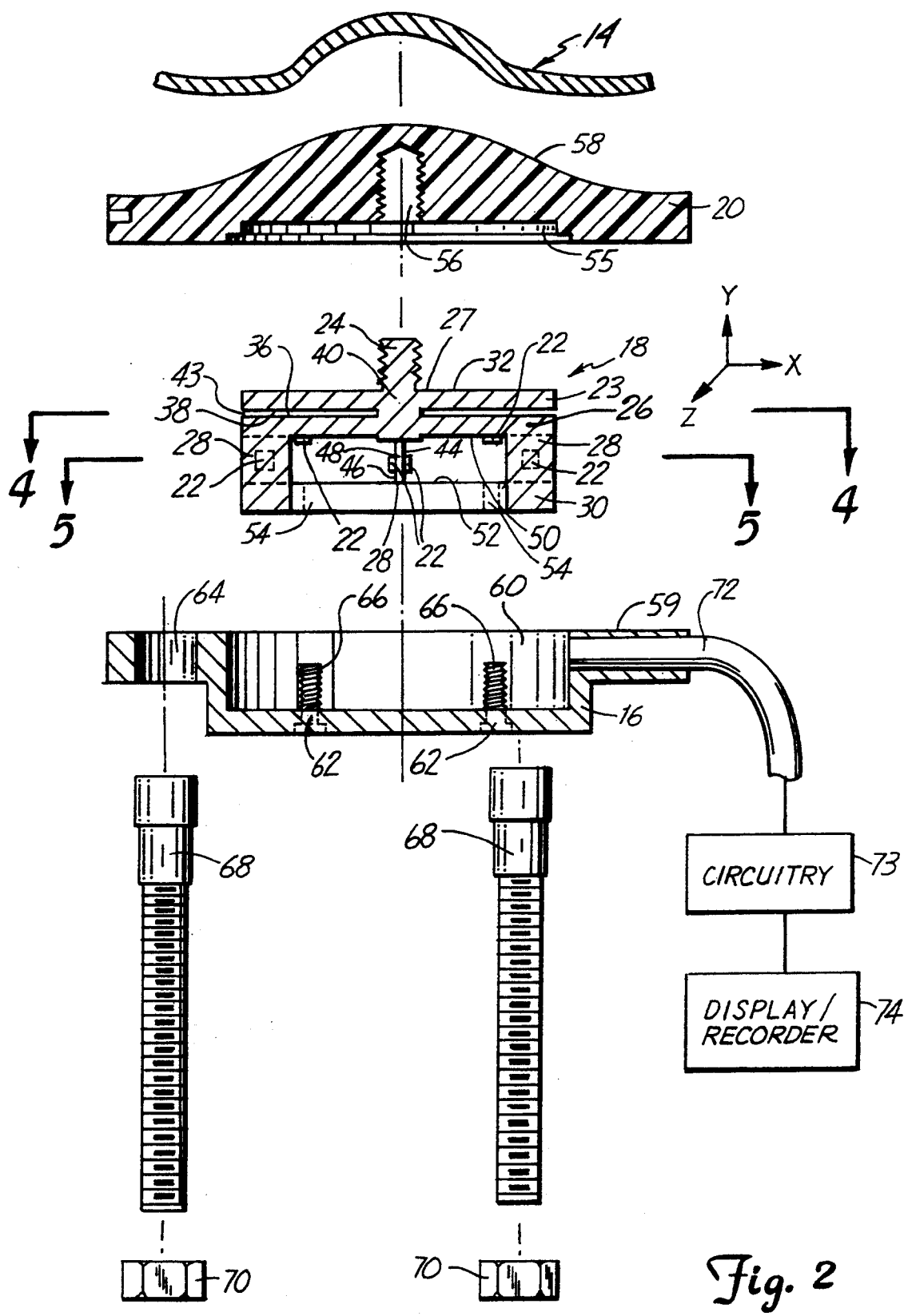
FIG. 2 is an exploded sectional view of the apparatus of the present invention and the artificial femoral attachment taken along the line 2—2 of FIG. 1.
Figure 3:
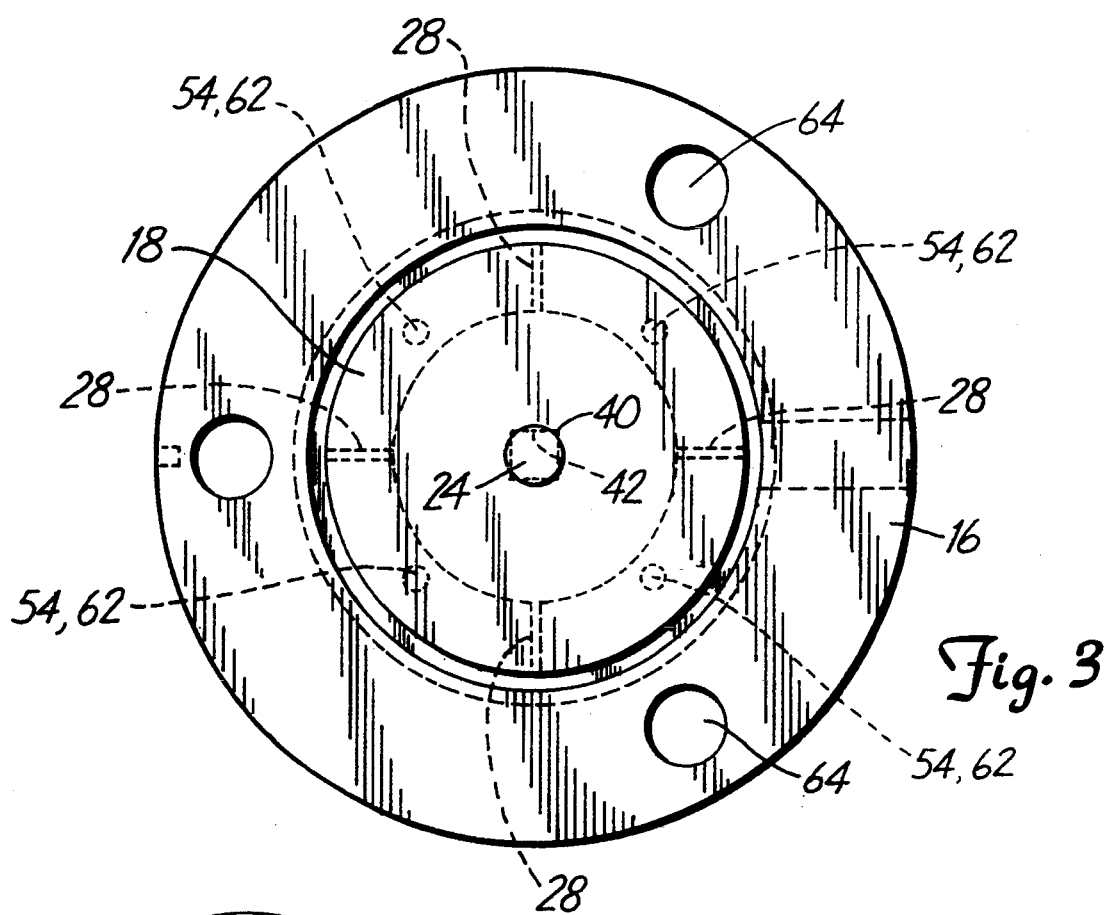
FIG. 3 is a top view of the apparatus of the present invention with the sensor cover removed.
Figure 4:
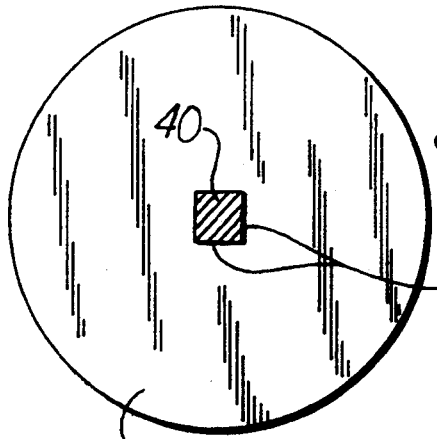
FIG. 4 is a sectional view of the apparatus of the present invention taken along the line 4—4 of FIG. 2.
Figure 5:
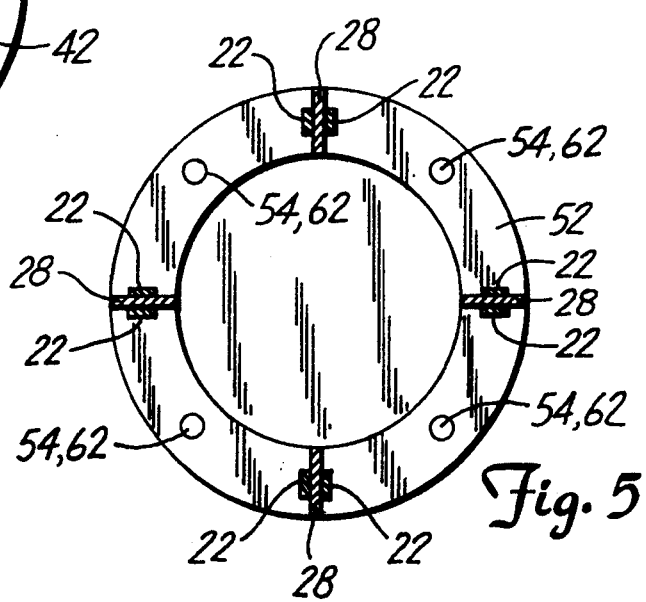
FIG. 5 is a sectional view of the apparatus of the present invention taken along the line 5—5 of FIG. 2.

A human knee 10 having a patella sensor 12 of the present invention inserted therein is shown in FIG. 1. The patella sensor 12 is shown inserted in a patella 13 and is in contact with an artificial femoral attachment 14. FIG. 1 also shows an artificial tibial attachment 15 used in total knee arthroplasty, which is attached to a resected tibia typically using a central stem or a plurality of smaller peripheral stems, not shown. The patella sensor 12, as shown in FIG. 2, comprises a base housing 16, a sensor 18, a sensor cover 20 and a plurality of strain gages 22.

The sensor 18 comprises a first disc 23 having a stud 24, and a second disc 26 equal in size to the first disc 23. The stud 24 extends from the center of a first side 27 of the first disc 23 and is threaded along its length. Four supports 28 extend between a base ring 30 and the second disc 26. The sensor 18 is fabricated from a suitable non-toxic material such as stainless steel, titanium or cobalt-chromium alloys.

The center of a first side 36 of the second disc 26 is attached to the center of a second side 38 of the first disc 23 by a square spacer plate 40. The spacer plate 40 has sides 42 that are substantially shorter than the diameter of the first disc 23 and the second disc 26. There is therefore a space 43 between the first disc 23 and the second disc 26.

Each of the four supports 28 has a rectangular cross section and has a first side 44, a second side 46, and two edge surfaces 48. The ends of the supports 28 are integral with the base ring 30 and the second disc 26, respectively. A second side 50 of the second disc 26 faces a first side 52 of the base ring 30. The base ring 30 has four threaded holes 54 equally spaced around it and positioned between the respective supports 28.

The sensor cover 20 has a contoured surface, as illustrated, a domed button shape that is substantially the same shape as that of a patellar insert. In addition, the sensor cover 20 is fabricated from polyethylene or other inert, somewhat resilient, low friction materials and has a bore 55 with a threaded portion 56. The sensor cover 20 is screwed onto the stud 24 and is tightened with a spanner wrench until it fits snugly over the stud 24 and the first disc 23 of the sensor 18. If desired, a suitable adhesive can be used to secure the sensor cover 20 to the surface 32. An outer surface 58 of the dome of the sensor cover 20 comes into contact with the femoral insert 14. Preferably, the position of the outer surface 58 relative to the remaining surfaces on the resected patella 13, and the outer surface 58 overall shape is similar to that of the patella 13 prior to resection. In other words, the mounted patella sensor 13 is similar to the natural patella prior to resection. The mounted patella sensor 12 and remaining patella 13 thus simulate the original patella. Using an implantable transducer assembly, direct and accurate loading between the patella and femur components of the knee can be obtained.

The base housing 16 is a stainless steel cup having a flange 59 and forming a circular recess 60 at its center. Four holes 62 are formed in the bottom of the base housing 16 and are equally spaced around the axis of the recess 60. Three holes 64 are equally spaced around the flange 59. The base ring 30 is fitted in the recess 60 such that the holes 62 in the recess 60 are aligned with the holes 54 in the base ring 30. A separate screw 66 is inserted through each hole 62 and threaded into an aligned hole 54 to secure the sensor 18 to the base housing 16.

The base housing 16 is attached to the knee 10 by three stainless steel cap screws 68 which are inserted through the holes 64 in the flange 59 of the base housing 16. Each cap screw 68 is further inserted through a hole drilled in the patella 13 and is secured by a nut 70. As illustrated in FIG. 1, the base housing 16 is supported on the patella 13 on a recessed, resected surface 69. The mounting arrangement as illustrated in FIG. 1 although suitable for a cadaver (in vitro) would not be preferred when it is desired to mount the patella sensor 12 in a human (in vivo).

The dome of the sensor cover 20 typically contacts the femoral attachment 14. As the knee 10 is flexed, the points at which the sensor cover 20 contacts the femoral attachment 14 will change as the position of the sensor cover 20 changes with respect to the femoral attachment 14. The forces acting between the sensor cover 20 and the femoral attachment 14 are transmitted through the sensor cover 20 to the sensor 18. The forces are then transmitted through the stud 24 and the spacer plate 40 to the second disc 26.

The directions of the three orthogonal components of the forces acting on the sensor cover 20 are represented by the directional axes X, Y, and Z shown in FIG. 2. The magnitudes of the components are measured by the twelve strain gages 22 which are mounted on the sensor 18. Four of the strain gages 22 are mounted on the second side 50 of the second disc 26 and two of the strain gages 22 are mounted on each of the supports 28.

The Y component of the forces acting on the sensor cover 20 causes a diaphragm like deflection of the edge supported second disc 26. This deflection is detected by the strain gages 22 mounted on the second disc 26. The X and Z components of the forces acting on the sensor cover 20 cause a movement of the second disc 26 relative to the base ring 30. This movement causes the supports 28 to flex in one or more directions parallel to the second disc 26 and the base ring 30, that is, in the plane of the X-Z axes. A strain gage 22 is mounted on each of the sides 44,46 of each support 28 to measure the flexure.

The amount of deflection of the second disc 26 and lateral flexure of each of the supports 28 is measured and converted to electrical signals by the strain gages 22 which are electrically connected to a plurality of wires, generally represented at 72. The wires 72 lead from the sensor 18 and are electrically connected to an apparatus that is capable of calculating the forces on the sensor cover 20 from the electrical signals sent by the strain gages 22. The strain gages 22 are connected in Wheatstone bridges which provide the signals indicating the magnitude of the force in the direction of each axis. Excitation and readout circuitry 73, shown schematically in FIG. 2, is used to provide information to either a display or to a recorder 74, as desired. Sensors, such as optical sensors, can be used in place of the strain gages 22 for sensing deflection of the second disc 26 and flexure of the supports 28. If desired, a radio transmitter can be built into the sensor with a suitable power supply for wireless transmission of the force data.

An annular space 75 is formed between the sensor cover 20 and the flange 59 of the base housing 16. The annular space 75 is necessary to prevent the forces acting on the sensor cover 20 from being transmitted directly to the base housing 16 which would render the strain gages 22 on the sensor 18 ineffective. The space 43 between the first disc 23 and the second disc 26 prevents the Y component of the forces acting on the sensor cover 20 from being transmitted directly through the supports 28 to the base housing 16 which would prevent deflection of the second disc 26 and render the strain gages 22 on the second disc 26 ineffective. The annular space 75 is sealed at an outer edge of the base housing 16 and the sensor cover 20.

Figure 6:
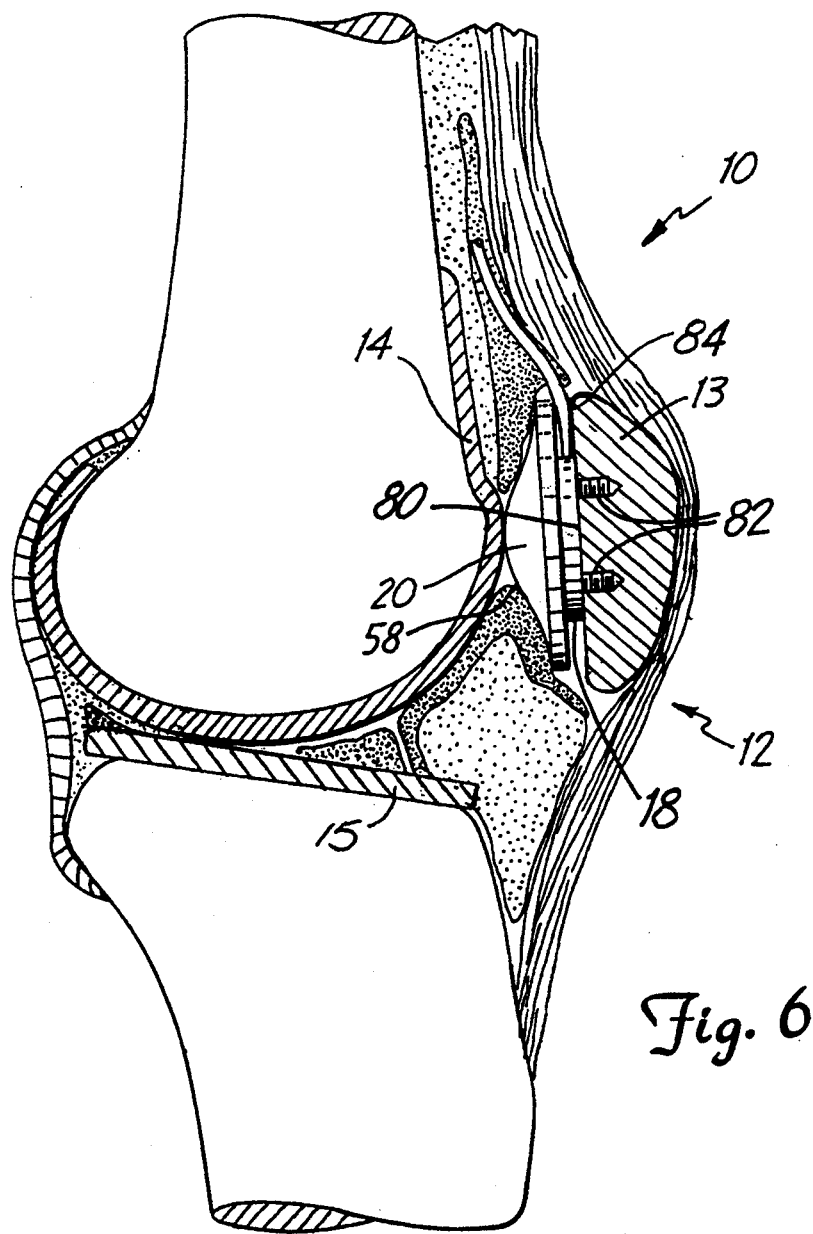
FIG. 6 is a side view of a second embodiment of the apparatus of the present invention inserted in a human knee.

Referring to FIG. 6, a second embodiment of the present invention mounts the sensor 12 directly to a resected surface 80 on the patella 13. Preferably, the resected surface 80 is flat being formed on the bone of the patella 13. The sensor 12 is mounted to the surface 80 using a suitable adhesive and, if desired, mounting studs 82 through the apertures 54. An annular space 84 provided between the surface 80 and an opposed surface of the sensor cover 20 insures proper operation of the patella sensor 12. Preferably, the mounted patella sensor 12 and remaining patella 13 simulate the original patella.

In summary, the present invention provides an implantable force transducer assembly for measuring patellofemoral forces. By implanting the transducer between the patella and the femur of the knee, direct and accurate measurement of all forces can be obtained. The data obtained assists in selecting the optimal method for implantation to achieve the best load distribution and fixation stability as well as provides data for designing the patellofemoral components of an artificial knee.

Although the present invention has been described with reference to preferred embodiments, workers skilled in the art will recognize that changes may be made in form and detail without departing from the spirit and scope of the invention.

What is claimed is:

1. A method for obtaining loading and boundary limits for the design of patellofemoral prosthetic components by measuring forces between a patella and a femur of a human knee, the method comprising:

resecting a portion of the patella to provide a mounting surface on the patella facing the femur;

mounting a first portion of a force transducer on the mounting surface;

forming a second portion of the force transducer to provide a femoral engaging surface of the force transducer that simulates an outer contour surface of the patella prior to the step of resecting positioned to engage a femoral surface of the femur, the force transducer providing a signal representing measured forces exerted between the resected patella and loads on the femoral engaging surface; and flexing the knee with the mounted force transducer being loaded between the femur and the patella to obtain force data representing the measured forces between the patella and the femur to determine design criteria for design of patella femoral prosthesis components.

2. The method of claim 1 wherein the step of resecting includes making the mounting surface flat.

3. The method of claim 2 wherein the step of mounting includes cementing the force transducer to the mounting surface.

4. The method of claim 1 wherein the step of mounting includes affixing mounting studs though the mounting surface and into the patella.

* * * * *